United States Patent [19]
Weisner et al.

[11] Patent Number: 5,262,944
[45] Date of Patent: Nov. 16, 1993

[54] METHOD FOR USE OF COLOR AND SELECTIVE HIGHLIGHTING TO INDICATE PATIENT CRITICAL EVENTS IN A CENTRALIZED PATIENT MONITORING SYSTEM

[75] Inventors: Steven J. Weisner, Lexington; James M. Grady, North Andover, both of Mass.; Wilhelm Meier, Herrenberg; Frank Weber, Plochingen, both of Fed. Rep. of Germany

[73] Assignee: Hewlett-Packard Company, Palo Alto, Calif.

[21] Appl. No.: 883,519

[22] Filed: May 15, 1992

[51] Int. Cl.$^5$ .................. A61B 5/00; G06F 15/42; G08B 23/00; G09G 1/28
[52] U.S. Cl. .................. 364/413.02; 128/712; 340/573; 340/870.09; 340/870.16; 364/413.03; 345/150
[58] Field of Search ............... 340/573, 701, 721, 720, 340/870.09, 870.16; 128/696, 710, 712; 364/413.02, 413.03, 413.04, 188, 189, 185

[56] References Cited

U.S. PATENT DOCUMENTS 4,191,349 3/1980 Lane .................. 340/721
4,648,028 3/1987 DeKlotz et al. .................. 364/188

OTHER PUBLICATIONS

"Large Screen Display Monitor," *CSIO Communications*, vol. 2, No. 4, pp. 70–71, Oct.–Dec. 1975, Chandigarh, India.

*Primary Examiner*—Glen R. Swann, III

[57] ABSTRACT

A centralized patient monitoring system includes a central station which receives patient information from bedside monitors. The patient information is presented on a video display screen and may include patient demographic information, physiological parameters and a waveform. The display screen is divided into sectors, with each sector containing information for one patient. When an alarm condition occurs at one of the bedside monitors, the alarm condition is transmitted to the central station and is displayed in the corresponding sector of the video display screen. In addition, the alarm condition is highlighted by changing the background in the alarming sector from its normal color, typically black, to a neutral color such as blue, which is easily distinguishable from the normal color and which does not obscure the patient information being displayed. The background of the sector is changed back to the normal color when the alarm is acknowledged by a user. The highlighted background is easily visible from a distance and provides a clear indication of unacknowledged alarms without obscuring other patient information.

17 Claims, 4 Drawing Sheets

METHOD FOR USE OF COLOR AND SELECTIVE HIGHLIGHTING TO INDICATE PATIENT CRITICAL EVENTS IN A CENTRALIZED PATIENT MONITORING SYSTEM

FIELD OF THE INVENTION

This invention relates to techniques for displaying patient critical events with other patient information in a centralized patient monitoring system and, more particularly, to techniques for highlighting patient critical events on a video display screen with a background color which is easily distinguishable from a normal background color and which does not obscure patient information.

BACKGROUND OF THE INVENTION

Centralized patient monitoring systems have been in use for a number of years. These systems are typically used in an intensive care unit (ICU), but are not limited to such use. A typical patient monitoring system includes a bedside monitor for each patient. The bedside monitor includes transducers for monitoring physiological parameters such as ECG, heart rate, blood pressure and any other parameters that may be important for a specific patient. The bedside monitors are connected to a central station that is located, for example, at a nurse station. The patient information gathered by the bedside monitors is displayed at the central station on a video display screen. The video display screen is typically divided into sectors, or areas, and patient information from one bedside monitor is displayed in each area. For example, the screen may contain four, six or eight sectors. The patient information displayed in each sector of the screen may include demographic information, such as name, bed number and ID number or physician, and physiological parameters being monitored by the bedside monitor. Typically, at least one of the physiological parameters is a waveform.

The patient monitoring system also has the ability to handle patient critical events, or alarms. For example, when one of the physiological parameters being monitored meets a predetermined alarm criteria, an alarm is generated by the bedside monitor and is transmitted to the central station. The alarm can be annunciated at the central station in various ways. According to one technique, an alarm text is displayed in the corresponding sector of the video display screen, and a small area surrounding the alarm text is highlighted in a alarm color. In addition, an audible alarm is generated by the central station. Alarms are typically classified into several categories. For example, a "red" alarm may indicate a life threatening patient condition, a "yellow" alarm may indicate a serious but non life threatening patient condition, and a "green" alarm may indicate an equipment malfunction.

It will be understood that it is extremely important to present the information on the video display screen of a patient monitoring system in a clear and unambiguous manner. When any confusion or misunderstanding occurs, the ability to respond to patient conditions quickly may be compromised. Thus, it is important that alarm conditions be clearly annunciated on the video display screen. The alarm condition should not obscure or detract from other patient information that is being displayed. Furthermore, the alarm condition should not be confused with other less serious alarms or with alarms which have already been attended to and acknowledged. The alarm condition should be visible from a distance, since the users of the system do not always sit directly in front of the video display screen.

Prior art systems have had various disadvantages with respect to the above requirements. For example, in the above described system, the alarm indication (including an alarm text on a small colored background) remains on the video display screen as long as the condition which gave rise to the alarm exists, even though a nurse may have attended to the patient. Thus, several alarm conditions may appear on the screen simultaneously. Some of the alarms may require attention, while others may have been attended to. The audible tone generated by the central station indicates only the highest level of alarm, not the number of such alarms or whether alarms of lower priority exist. Thus, there is the possibility of confusion as to which alarms, if any, require service and which alarms have been serviced.

One known technique for highlighting critical events is to cause an alarm indication or critical physiological parameter to flash. A flashing condition is very effective in attracting the attention of the user. However, the flashing condition may be so attention getting that it detracts from other important information being displayed on the screen. Furthermore, when several items simultaneously flash on the screen, confusion may arise. Another known technique for annunciating alarm conditions is to replace all or part of the multiple patient display with an enlarged display pertaining to the alarm condition. While this approach is clearly effective in highlighting the alarm condition, it obscures information pertaining to other patients and is not effective when more than one alarm condition exists simultaneously.

It is thus desired to provide a technique for displaying patient information on a video display screen wherein alarm conditions are clearly annunciated without obscuring other patient information. The display must indicate which alarm conditions have been attended to and which alarm conditions require attention. The display must also indicate the severity of the alarm and must indicate alarm conditions from a distance.

It is a general object of the present invention to provide improved methods and apparatus for displaying patient information and patient critical events in a centralized monitoring system.

It is another object of the present invention to provide centralized patient monitoring methods and apparatus wherein patient critical events are clearly highlighted until acknowledged by a user.

It is a further object of the present invention to provide centralized patient monitoring methods and apparatus wherein patient critical events are highlighted in a color that is easily distinguishable from colors used under normal conditions and which does not obscure patient information.

It is yet another object of the present invention to provide centralized patient monitoring methods and apparatus wherein patient critical events are highlighted in a manner that is easily identified from a distance.

It is a further object of the present invention to provide methods and apparatus for clearly presenting patient information and patient critical events on a video display screen in a centralized patient monitoring system.

SUMMARY OF THE INVENTION

According to the present invention, these and other objects and advantages are achieved in a method for highlighting patient critical events in a centralized patient monitoring system. A central station of the monitoring system has a video display screen. The central station receives patient information and patient critical events, or alarms, from a plurality of bedside monitors. Patient information and alarms are displayed in discrete areas, or sectors, of the video display screen. Each of the discrete areas corresponds to one of the bedside monitors. Each of the discrete areas has a background of a first color when an alarm has not been received from the corresponding bedside monitor. An alarm that has not been acknowledged by a user is highlighted by changing the background in the corresponding area of the video display screen from the first color to a second color which is easily distinguishable from the first color and which does not obscure the patient information being displayed. In a preferred embodiment, the first background color is black and the second background color which highlights alarms is blue.

When the alarm is acknowledged by a user, typically by pressing a button at the central station or at the corresponding bedside monitor, the background in the corresponding area of the video display screen is changed from the second color to the first color. Thus, the video display screen provides a clear indication of all alarms that have not been acknowledged.

Information as to each alarm is displayed in a portion of the area on the video display screen corresponding to the bedside monitor from which the alarm was received. The alarm information includes text identifying the alarm on a background of a predetermined color which indicates the severity of the alarm. The alarm information remains on the video display screen until the condition no longer exists.

The patient information displayed on the video display screen typically includes demographic information and physiological parameters obtained by the bedside monitors. The physiological parameters typically include a waveform, such as an ECG waveform. According to a further feature of the invention, the color of the patient information is selectable for different patients or for different physiological parameters. Thus, the patient information for the patients assigned to a particular nurse can be displayed in a selected color. Also, different physiological parameters can be displayed in different colors.

According to another aspect of the invention, there is provided a central station for displaying patient information in a centralized patient monitoring system. The central station comprises a video display screen, means for receiving patient information and alarms from a plurality of bedside monitors, means for displaying the patient information in discrete areas on the video display screen, each of the discrete areas corresponding to a single bedside monitor, including means for displaying the patient information in each of the discrete areas on a background of first neutral color when the central station has not received an alarm from the corresponding bedside monitor, and means for highlighting an alarm received from one of the bedside monitors by changing the background in the corresponding area of the video display screen from the first neutral color to a second neutral color which is easily distinguishable from the first neutral color and which does not obscure the patient information.

BRIEF DESCRIPTION OF THE DRAWINGS

For a better understanding of the present invention, together with other and further objects, advantages and capabilities thereof, reference is made to the accompanying drawings, which are incorporated herein by reference and in which.

DETAILED DESCRIPTION OF THE INVENTION

Figure 1:
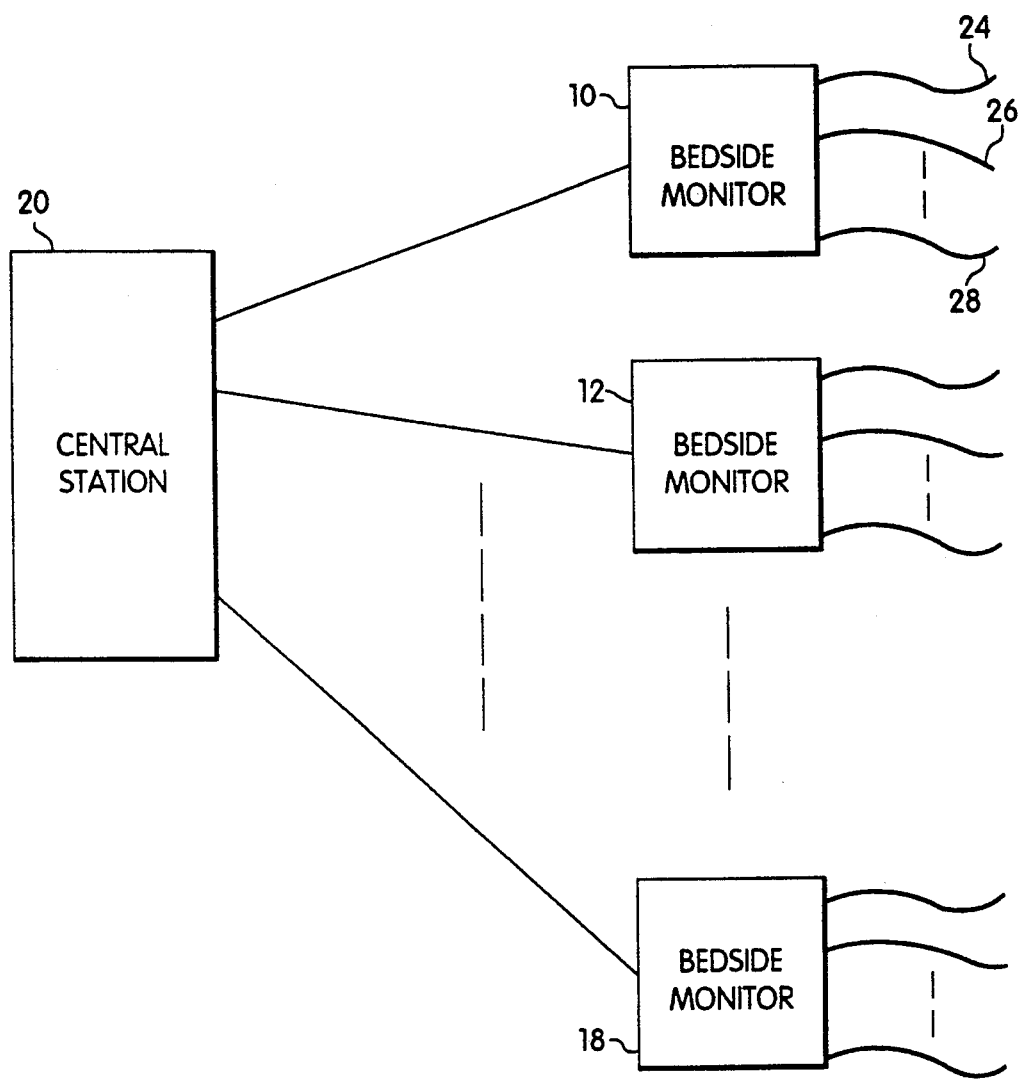
FIG. 1 is a block diagram of a patient monitoring system suitable for incorporation of the present invention.

A centralized patient monitoring system suitable for incorporation of the present invention is shown in FIG. 1. Bedside monitors 10, 12, . . . , 18 are connected to a central station 20. Each bedside monitor is located next to a patient bed and includes transducers 24, 26, . . . , 28 which may be attached to the patient. Each bedside monitor monitors the condition of the patient and transmits patient information to central station 20. The information includes demographic information, such as the patient's name, bed number, and the patient's ID number or physician, physiological parameters such as heart rate, ECG, blood pressure and the like, and patient critical events, or alarms, which occur when one of the physiological parameters meets a predetermined criteria. The bedside monitors 10, 12, . . . , 18 typically include a video display of individual patient information. An example of a bedside monitor is a Model M1176B, manufactured and sold by Hewlett Packard Company.

The central station 20 is typically located at a nurse station in an ICU or similar critical care unit. Central station 20 receives selected information from the bedside monitors 10, 12 . . . , 18 and presents a video display of the selected patient information. The central station 20 can typically display information from up to eight bedside monitors.

Figure 2:
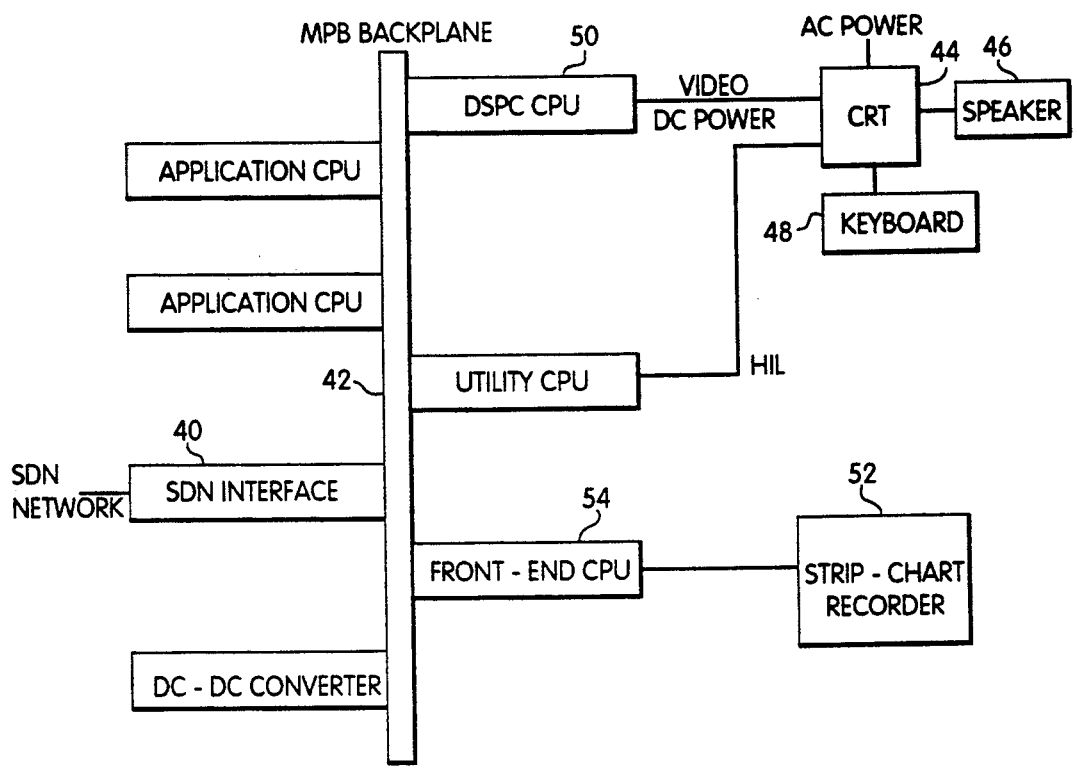
FIG. 2 is a block diagram of the central station of FIG. 1.
Figure 5:
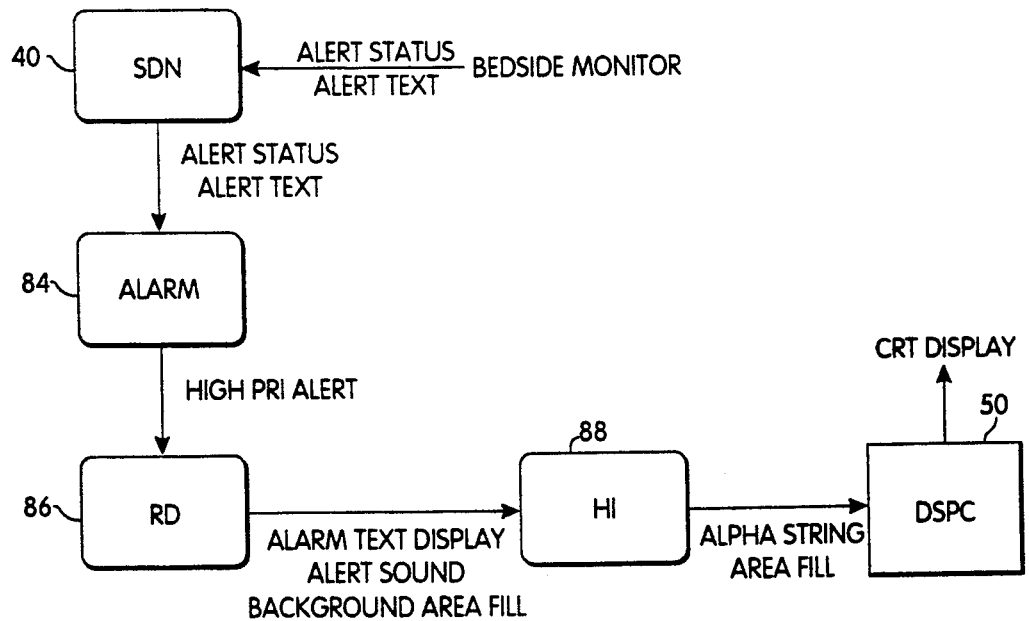
FIG. 5 is a block diagram that illustrates the flow of an alarm message through the central station software.

A block diagram of the central station 20 is shown in FIG. 2. Patient information is received from the bedside monitors through a serial distribution network (SDN) in an SDN interface 40. The SDN interface 40 is connected to a message passing bus (MPB) 42. A color CRT, or video display screen, 44, a speaker 46 and a keyboard 48 are connected to a display controller 50 which receives information from the message passing bus 42. A strip chart recorder 52 is connected to a front end CPU 54 which receives information from message passing bus 42. The overall structure of the central station shown in FIG. 2 is similar to that of the Model 78560 manufactured and sold by Hewlett Packard Company. However, the Model 78560 does not include a color video display screen and does not annunciate patient critical events in the manner described below.

Figure 3:
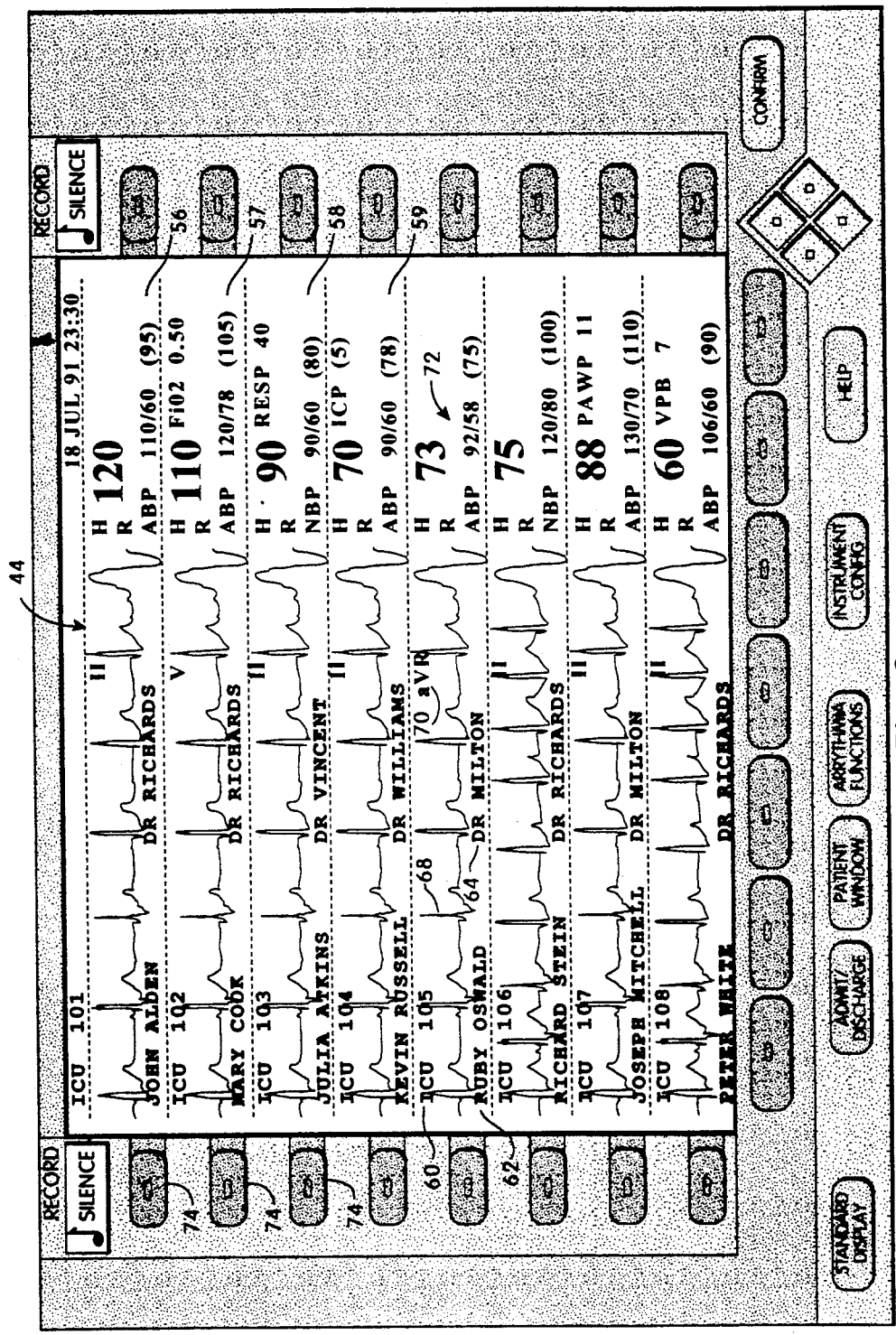
FIG. 3 shows a display of patient information in the absence of an alarm.

An example of a patient information display on the video display screen 44 of central station 20 is shown in FIG. 3. In the example of FIG. 3, no patient critical events, or alarms, have occurred. The display is divided into several areas called "sectors". Typically, the sectors have equal areas. Each sector contains a waveform, physiological data, alarms and patient demographic information for one bed. In the example of FIG. 3, eight sectors 56, 57, 58, 59, etc. are arranged vertically, and each sector is a rectangular area of the video display screen. It will be understood that other sector arrangements can be utilized. For example, the layout can include six beds arranged vertically, four beds arranged vertically, eight beds split into two columns of four beds each, and the like. Typically, one sector is assigned to each bedside monitor. However, more than one sector can be assigned to one bedside monitor if desired.

The display contains patient demographic information in each sector. A bed label 60, a patient name 62 and an additional field 64 is displayed for each patient. The patient demographic data is displayed in dense characters (12 alpha pixels wide by 16 pixels high) in full bright white color. The additional field 64 can be the patient ID, heart rate limits, physician's name, or the like. Paced patients have a paced indicator 66.

Each sector also includes a waveform 68 which starts on the left side of each sector. The waveform 68 is a real time copy of a waveform from the corresponding bedside monitor. The waveform 68 is typically an ECG waveform, but any waveform from the bedside monitor can be displayed. The waveform 68 is preferably displayed in green. However, the user can select another color for each waveform. The waveform amplitude is adjusted so that it can be displayed within one sector without clipping. A waveform label 70 is located above each waveform to the right of the bed label 60.

A parameter area 72 at the right side of each sector displays real time physiological parameters, indicates the parameter alarm state and the validity of the physiological data. All information is derived from the corresponding bedside monitor. A parameter includes a parameter label, a single or triple value parameter value and an alarm suspend or questionable data indicator. Spaces are typically provided for heart rate, two single parameter strings and one triple value parameter string. Parameters are typically displayed in green.

The video display screen is surrounded by a bezel, including buttons which permit control of the central station. Buttons 74 adjacent to each sector permit alarms to be acknowledged, or silenced, by the user as described below.

Figure 4:
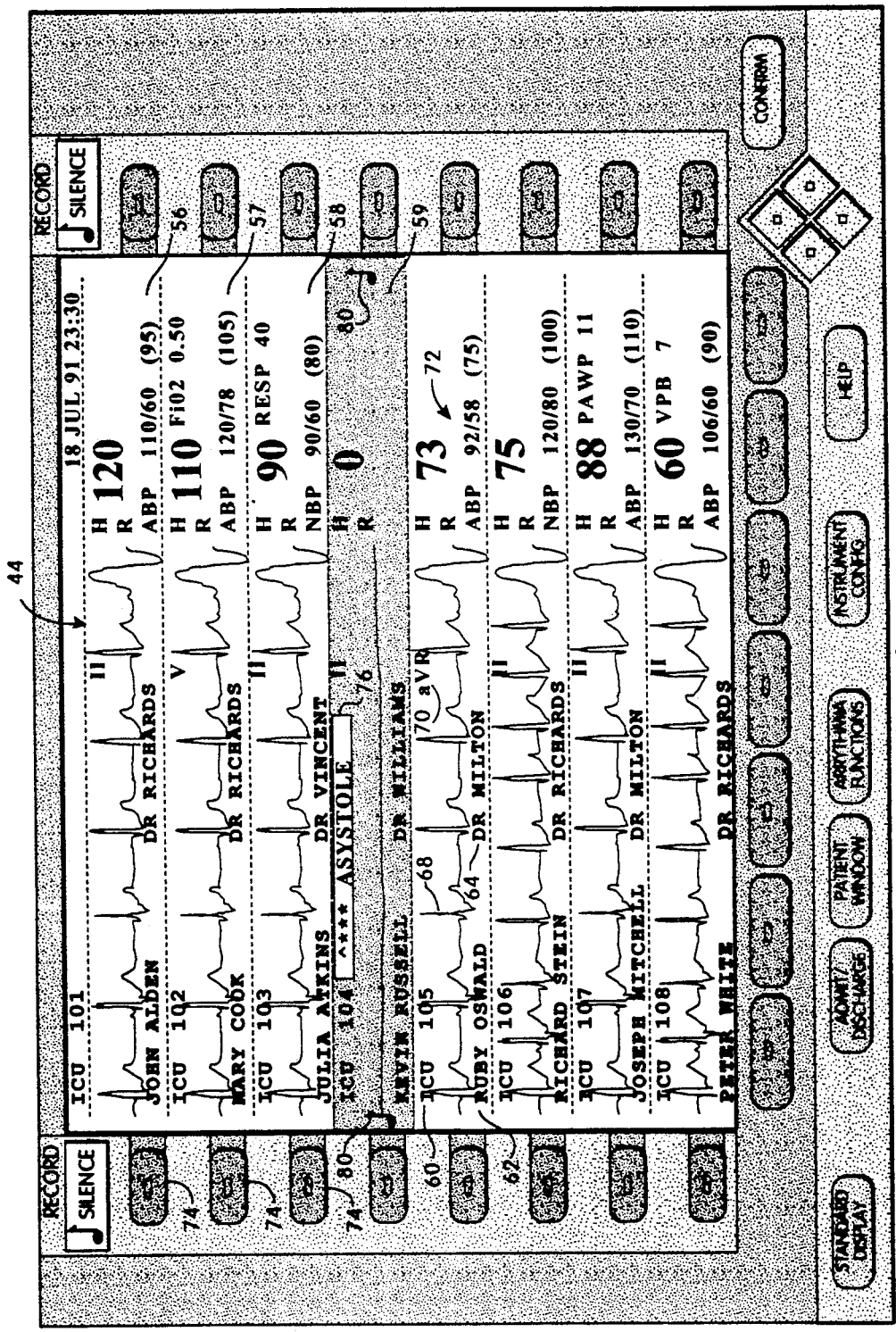
FIG. 4 shows a display of patient information with an alarm, illustrating highlighting in accordance with the present invention.

Central station 20 displays patient critical events (alarms) and equipment inoperative (inop) messages generated by the bedside monitors as shown in FIG. 4. A field above the waveform 68 and to the right of the bed label 60 in each sector is used to display both alarm and equipment inoperative text messages. A patient alarm 76 is shown in FIG. 4. In the example of FIG. 4, the alarm 76 is a red alarm with the text "ASYSTOLE" in white letters on a red background. As described below, annunciation of the alarm 76 also includes displaying note characters 80 in white at the left and right sides of the sector and changing the background color of the sector from black to blue. The central station 20 displays only the highest level alarm or equipment inoperative condition occurring for a bed. When there is more than one alarm or equipment inoperative condition pending for a bed at any one time, an up arrow appears immediately preceding the alarm text message. The up arrow is removed when only one alarm/equipment inoperative condition exists for the bed.

Red alarms are displayed as white text on a red, full bright background with "* * *" preceding the alarm text. Yellow alarms are displayed as black text on a yellow, half bright background with "**" preceding the alarm text. Green inops are displayed as black text on a green, half bright background with no leading stars. The distinction between red and yellow alarms and inops is defined by the bedside monitor or other equipment which generates the alarms.

When a red or yellow alarm or an inop condition occurs at one of the bedside monitors, the following actions are taken by the central station 20. 1) The associated alarm or inop text field is displayed on the corresponding sector of the central station video display screen in the alarm color. The alarm color covers a relatively small background area that is somewhat larger than the alarm text. 2) For red or yellow level alarms, the background color of the sector for the alarming bed is changed from black to blue. The entire background area of the sector is changed from black to blue. In FIG. 4, the background of sector 59 is blue because of the alarm condition. The patient information, including demographics, physiological parameters, waveform and alarm information, is not changed or obscured by the blue background. 3) A note character 80 is displayed on the left and right sides of the sector. 4) A standard alarm sound is generated by speaker 46 according to the following rules: a) only one alarm sound can be generated on the central station at one time, b) the red alarm sound is generated if any bedside monitor has an unsilenced red alarm condition, c) the yellow alarm sound is generated if any bedside monitor has an unsilenced yellow alarm condition and no other bedside monitors have an unsilenced red alarm condition, and d) the equipment inoperative alarm sound is given if any bedside monitor has an unsilenced equipment inoperative condition and no other beds have an unsilenced red or yellow alarm condition. 5) A strip chart recording of the bedside waveform is directed to the central station recorder 52.

The blue background of the sector appears for a bed as long as that alarm is generating a sound. The note characters 80 also appear while the alarm is generating the sound. When the alarm is silenced, or acknowledged, by a user, then the background is changed from blue to black and the note characters are erased.

If the silenced alarm/inop sound is currently the highest priority sound being annunciated at the central station, then the next highest priority sound, if any, is annunciated according to the above rules. The alarm/inop message remains on the video display screen as long as the alarm/inop condition remains active for that bed.

The use of the blue background to highlight alarms has several important features. The blue background is easily distinguished from the black background used on nonalarming sectors. Since the entire sector is highlighted with a blue background, the alarm condition can be easily identified from a distance. When the user becomes familiar with the relative positions of the beds on the video display screen, the alarming bed can be identified immediately and appropriate action can be taken. When the alarm has been responded to and acknowledged, either at the bedside monitor or at the central station, the blue background is changed to black. Thus, while the alarm text and associated color remains on the video display screen as long as the alarm condition exists, the highlighting of sectors with unacknowledged alarms makes it immediately apparent to the user which alarms are new and which alarms have been acknowledged.

As described above, the normal background color is black, and unacknowledged alarms are highlighted with a blue background. It will be understood that other color combinations can be used within the scope of the invention. In general, the normal and highlighted background colors should be "neutral" so that they do not obscure the patient information being displayed. Furthermore, the normal and hiqhlighted colors should be easily distinguishable from each other. Other suitable background/highlight color combinations include black/light gray, black/cyan, dark gray/blue and dark blue/light blue.

Alarm information is acquired from the bedside monitors on the serial distribution network. The alarm information is in the form of two information packets labeled alert status and alert text. The alert status packet contains bed identification, alarm text severity, alert sound severity, alarm on/off indicators and change counters. The alert text packet contains bed identification, an 18 character alert text field and alarming parameter source identification. The alert status and alert text packets enter the central station 20 through the SDN interface 40 and are broadcast on the message passing bus 42.

An alarm module 84 handles all alert status and alert text packets for all beds being monitored by the central station. The alarm module 84 determines the highest priority alert information for each bed and broadcasts this message (high priority alert) on the message passing bus 42 to a resting display module 86.

The resting display module 86 receives the high priority alert message for every monitored bed and determines the highest priority sounds among all the beds. The single highest priority alert sound is sent to a human interface module 88 which in turn forwards the message to the display controller 50. The display controller 50 drives both the CRT display and the sound generator. The sound is annunciated from the speaker 46. The resting display module 86 also presents the alert text field for each bed in the appropriate location on the bed sector.

The alert text field is presented to the display controller 50 in the appropriate alarm severity as indicated by the original alert status message. The alarm messages are presented on the video display as described above.

The resting display module 86 also highlights the alarming sector or sectors in a neutral blue color by sending an area fill command specifying the color and a display plane (alpha graphics plane 2) that is different from the display planes used to show the waveform (wave plane 1), parameters, alarm text and patient demographics (alpha graphics plane 1). The display controller 50 mediates the three planes by ORing the signals together to present a single image on the video display screen 44.

As noted above, the blue background highlighting is displayed only during the period when the alert sound severity indicates a red or yellow sound. When the sound has been silenced (acknowledged by the user), at either the bedside monitor or at the central station, the background highlighting is removed by sending an area fill message in color black, alpha-graphics plane 2, to the human interface module and in turn to the display controller 50.

Typically, the patient demographic information is displayed in white, and patient waveform and physiological parameter information is displayed in green. According to a further feature of the central station 20, the color of the patient information can be selected individually by bed. Thus, for example, all patients assigned to one nurse can be displayed in one color and the patients assigned to another nurse can be displayed in a second color, etc. According to yet another feature, the display colors can be selected by physiological parameter. Thus, for example, all heart rate parameters can be displayed in one color, blood pressure parameters can be displayed in a second color, etc.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for displaying patient information in a patient monitoring system so as to clearly identifying an alarm, comprising the steps of:

displaying patient information received from a plurality of bedside monitors on a video display screen at a central station, said video display screen having a discrete areas, each of said discrete areas corresponding to a single bedside monitor, said patient information being displayed in each area on a background of a first neutral color when the central station has not received an alarm from the corresponding bedside monitor;

when the central station receives an alarm from one of the bedside monitors, highlighting the alarm by changing the background in the area of the video display screen corresponding to the bedside monitor from which the alarm was received from said first neutral color to a second neutral color which is easily distinguishable from said first neutral color and which does not obscure said patient information; and changing the background in the area of the video display screen corresponding to the bedside monitor from which the alarm was received from said second neutral color to said first neutral color when the alarm is acknowledged by a user, even when the alarm still exists.

2. A method as defined in claim 1, wherein the patient information is displayed on a background of black in the absence of an alarm and wherein the patient information is displayed on a background of blue when an alarm is received and has not been acknowledged.

3. A method as defined in claim 1 further including the step of displaying alarm information in an alarm portion of the area of the video display screen corresponding to the bedside monitor from which the alarm was received, said alarm information including text identifying the alarm on a background of a predetermined alarm color.

4. A method as defined in claim 3 wherein the alarm information is displayed on the video display screen until the alarm is no longer present.

5. A method as defined in claim 3 wherein said predetermined alarm color is selected from red, yellow and green depending on the type of alarm.

6. A method as defined in claim 1 wherein the step of displaying patient information includes displaying patient demographic information, patient physiological information and a waveform.

7. A method as defined in claim 1 further including the step of displaying a character in the area of the video display screen corresponding to the bedside monitor from which the alarm was received, said character being displayed until the alarm is acknowledged by the user.

8. A central station for displaying patient information in a centralized patient monitoring system, comprising:
   a video display screen;
   means for receiving patient information in discrete areas on said video display screen, each of said discrete areas corresponding to a single bedside monitor, including means for displaying said patient information in each of said discrete areas on a background of a first neutral color when the central station has not received an alarm from the corresponding bedside monitor; and
   means for highlighting an alarm received from one of the bedside monitors by changing the background in the area of the video display screen corresponding to the bedside monitor from which the alarm was received from said first neutral color to a second neutral color which is easily distinguishable from said first neutral color and which does not obscure said patient information, said means for highlighting including means for changing the background in the area of the video display screen corresponding to the bedside monitor from which the alarm was received from said second neutral color to said first neutral color when the alarm is acknowledged by a user, even when the alarm still exists.

9. A central station as defined in claim 8 wherein said first neutral color comprises black and said second neutral color comprises blue.

10. A central station as defined in claim 8 further including means for displaying alarm information in a predetermined region of each of said discrete areas, said alarm information including text identifying the alarm on a background of a preselected alarm color.

11. A central station as defined in claim 10 further including means for generating an audible indication of said alarm.

12. A method for highlighting patient critical events in a centralized patient monitoring system, comprising the steps of:
   providing a central station having a video display screen, said central station receiving patient information and patient critical events from a plurality of bedside monitors;
   displaying said patient information and said patient critical events in discrete areas of said video display screen, each of said discrete areas corresponding to one of said bedside monitors, each of said discrete areas having a background of a first color when a patient critical event has not been received from the corresponding bedside monitor and when a patient critical event has been acknowledged by a user;
   highlighting a patient critical event that has not been acknowledged by a user by changing the background in the area of the video display screen corresponding to the bedside monitor from which the patient critical event was received from said first color to a second color which is easily distinguishable from said first color and which does not obscure said patient information being displayed; and
   changing the background in the area of the video display screen corresponding to the bedside monitor from which the patient critical event was received from said second color to said first color when the patient critical event is acknowledged by a user, even when the patient critical event still exists.

13. A method as defined in claim 12 wherein the step of displaying patient information includes the step of displaying patient information in colors that are selectable for different patients.

14. A method as defined in claim 12 wherein the step of displaying patient information includes displaying patient physiological parameters in colors that are selectable for different physiological parameters.

15. A method for highlighting patient critical events on a video display of patient information, comprising the steps of:
   displaying patient information and patients critical events in discrete areas of a video display screen, each of said discrete areas corresponding to a single patient, each of said discrete areas having a background of a first color when a patient critical event has not been received;
   highlighting a patient critical event by changing the background in the area of the video display screen corresponding to the patient for which the patient critical event occurred from said first color to a second color which is easily distinguishable from said first color and which does not obscure said patient information; and
   changing the background in the area of the video display screen corresponding to the patient for which the patient critical event occurred from said second color to said first color when the patient critical event is acknowledged by a user, even when the patient critical event still exists.

16. A method as defined in claim 15 wherein the step of changing the background includes changing the background from back to blue.

17. A central station for displaying patient information in a centralized patient monitoring system, comprising:
   a video display monitor including a video display screen;
   an interface unit for receiving patient information and alarms from a plurality of bedside monitors; and
   a display controller responsive to the patient information and alarms received by said interface unit for displaying said patient information and alarms in discrete areas on said video display screen, said display controller including means for displaying said patient information in each of said discrete areas on a background of a first neutral color when the central station has not received an alarm from the corresponding bedside monitors, for highlighting an alarm received from one of the bedside monitors by changing the background in the area of the video display screen corresponding to the bedside monitor from which the alarm was received from said first neutral color to a second neutral color which is easily distinguishable from said first neutral color and which does not obscure said patient information, and for changing the background in the area of the video display screen corresponding to the bedside monitor from which the alarm was received from said second neutral color to said first neutral color when the alarm is acknowledged by a user, even when the alarm still exists.

* * * * *